United States Patent
Hwang et al.

(10) Patent No.: US 9,615,890 B2
(45) Date of Patent: Apr. 11, 2017

(54) SURGICAL ROBOT SYSTEM AND METHOD OF CONTROLLING THE SAME

(71) Applicant: Samsung Electronics Co., Ltd., Suwon-si (KR)

(72) Inventors: Won Jun Hwang, Seoul (KR); Kyung Shik Roh, Seongnam-si (KR); Suk June Yoon, Seoul (KR); Seung Yong Hyung, Yongin-si (KR)

(73) Assignee: Samsung Electronics Co., Ltd., Gyeonggi-Do (KR)

(*) Notice: Subject to any disclaimer, the term of this patent is extended or adjusted under 35 U.S.C. 154(b) by 442 days.

(21) Appl. No.: 13/965,460

(22) Filed: Aug. 13, 2013

(65) Prior Publication Data

US 2014/0288413 A1 Sep. 25, 2014

(30) Foreign Application Priority Data

Mar. 21, 2013 (KR) .................. 10-2013-0030239

(51) Int. Cl.
*A61B 5/05* (2006.01)
*A61B 34/37* (2016.01)
*A61B 34/30* (2016.01)
*A61B 90/00* (2016.01)

(52) U.S. Cl.
CPC .............. *A61B 34/37* (2016.02); *A61B 34/30* (2016.02); *A61B 90/361* (2016.02); *A61B 2090/364* (2016.02); *A61B 2090/367* (2016.02)

(58) Field of Classification Search
USPC ........................................................ 600/424
See application file for complete search history.

(56) References Cited

U.S. PATENT DOCUMENTS

| 6,148,100 | A  | * | 11/2000 | Anderson et al. | 382/153 |
| 2002/0061131 | A1 | * | 5/2002 | Sawhney et al. | 382/154 |
| 2004/0039485 | A1 | * | 2/2004 | Niemeyer et al. | 700/245 |
| 2006/0171573 | A1 | * | 8/2006 | Rogers | 382/128 |
| 2009/0088634 | A1 | * | 4/2009 | Zhao et al. | 600/427 |
| 2009/0129545 | A1 | * | 5/2009 | Adler et al. | 378/65 |
| 2009/0245600 | A1 | * | 10/2009 | Hoffman et al. | 382/128 |
| 2012/0197464 | A1 | * | 8/2012 | Wang et al. | 701/2 |

FOREIGN PATENT DOCUMENTS

| KR | 10-2007-0061011 | 6/2007 |
| KR | 10-2011-0118639 | 10/2011 |
| WO | 2010/084707 | 7/2010 |

* cited by examiner

*Primary Examiner* — Joel F Brutus
(74) *Attorney, Agent, or Firm* — Harness, Dickey & Pierce, P.L.C.

(57) ABSTRACT

A surgical robot system includes a slave system to perform a surgical operation on a patient and an imaging system that includes an image capture unit including a plurality of cameras to acquire a plurality of affected area images, an image generator detecting an occluded region in each of the affected area images acquired by the plurality of cameras, removing the occluded region therefrom, warping each of the affected area images from which the occluded region is removed, and matching the affected area images to generate a final image, and a controller driving each of the plurality of cameras of the image capture unit to acquire the plurality of affected area images and inputting the acquired plurality of affected area images to the image generator to generate a final image.

8 Claims, 11 Drawing Sheets

SURGICAL ROBOT SYSTEM AND METHOD OF CONTROLLING THE SAME

CROSS-REFERENCE TO RELATED APPLICATIONS

This application claims the priority benefit of Korean Patent Application No. 10-2013-0030239, filed on Mar. 21, 2013 in the Korean Intellectual Property Office, the disclosure of which is incorporated herein by reference.

BACKGROUND

1. Field

The following description relates to a surgical robot system to restore occluded regions, which are hidden regions of a surgical region of a patient, and a method of controlling the same.

2. Description of the Related Art

Minimally invasive surgery generally refers to surgery capable of minimizing an incision size and recovery time. Whereas laparotomy uses relatively large surgical incisions through a part of a human body (e.g., the abdomen), in minimally invasive surgery, after forming at least one small incision hole (or invasive hole) of 0.5 cm to 1.5 cm through the abdominal wall, an operator inserts an endoscope and surgical instruments through the incision hole, to perform surgery while viewing images provided by the endoscope.

Compared to laparotomy, such minimally invasive surgery causes less post-operative pain, faster recovery of bowel movement, earlier restoration of ability to eat, shorter hospitalization, faster return to daily life, and better cosmetic effects due to the small incision size. Due to these properties, minimally invasive surgery is used for cholecystectomy, prostatic carcinoma surgery, hernia repair, and the like, and applications thereof continue to grow.

In general, a surgical robot used in minimally invasive surgery includes a master device and a slave device. The master device generates a control signal in accordance with manipulation by a doctor and transmits the control signal to the slave device. The slave device receives the control signal from the master device and performs manipulation for surgery of a patient. The master device and the slave device may be integrated with each other, or may be separately arranged in an operating room.

The slave device includes at least one robot arm. Surgical instruments are mounted on an end of the robot arm.

In such minimally invasive surgery using a surgical robot, surgery is performed by use of surgical instruments of a slave device which are inserted into a human body. In this regard, the same surgical environment as conventional surgery needs to be provided to a manipulator manipulating a master device. Thus, surgical instruments corresponding to arms of an operator are disposed under the operator's field of vision. Accordingly, surgical instruments may obstruct the view of a surgical region.

SUMMARY

Therefore, the following disclosure describes a surgical robot system capable of displaying an affected area that does not have occluded regions during surgery and a method of controlling the same.

Additional aspects of the invention will be set forth in part in the description which follows and, in part, will be obvious from the description, or may be learned by practice of the invention.

In accordance with an aspect of the present disclosure, a surgical robot system includes a slave system to perform a surgical operation on a patient and an imaging system that includes an image capture unit including a plurality of cameras to acquire a plurality of affected area images, an image generator detecting an occluded region in each of the affected area images acquired by the plurality of cameras, removing the occluded region therefrom, warping each of the affected area images from which the occluded region is removed, and matching the affected area images to generate a final image, and a controller driving each of the plurality of cameras of the image capture unit to acquire the plurality of affected area images and inputting the acquired plurality of affected area images to the image generator to generate a final image.

In accordance with an aspect of the present disclosure, a method of controlling a surgical robot includes acquiring a plurality of affected area images using a plurality of cameras, detecting an occluded regions present in each of the acquired affected area images, removing the detected occluded regions from each of the affected area images, warping each of the affected area images from which the occluded regions are removed, and generating a final image by matching the warped affected area images.

In accordance with an aspect of the present disclosure, a surgical robot includes an image capture unit acquiring a plurality of images of an area from different locations on the surgical robot, and an image generator receiving the acquired images, detecting an occluded region in at least one of the acquired images, removing the occluded region, warping the image from which the occluded region is removed, and matching the acquired images with the warped image to generate a final image.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

The aspects, particular advantages, and novel features of the embodiments of the present invention will become apparent with reference to the following detailed description and embodiments described below in detail in conjunction with the accompanying drawings. In the drawings, the same or similar elements are denoted by the same reference numerals even though they are depicted in different drawings. In the following description of the embodiments, a detailed description of known functions and configurations incorporated herein will be omitted when it may make the subject matter of the embodiments rather unclear. Herein, the terms first, second, etc. are used simply to discriminate any one element from other elements, and the elements should not be limited by these terms.

Hereinafter, the embodiments will be described in detail with reference to the accompanying drawings.

According to the present embodiment, a surgical robot system including a slave system and a master system that remotely controls the slave system is exemplarily described. However, any surgical robot system in which an operator directly controls a slave system may be used.

Figure 1:
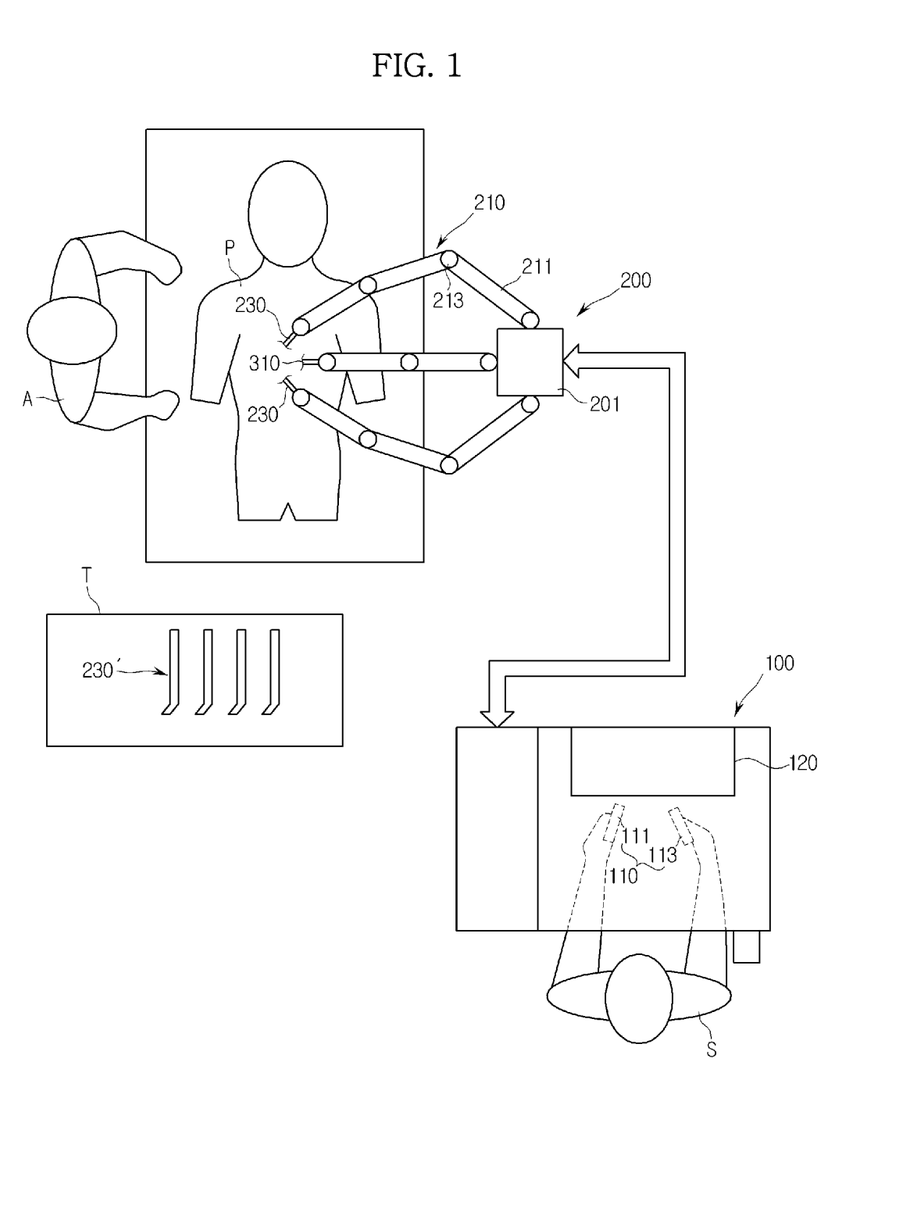
FIG. 1 is a view schematically illustrating a surgical robot system.
Figure 2:
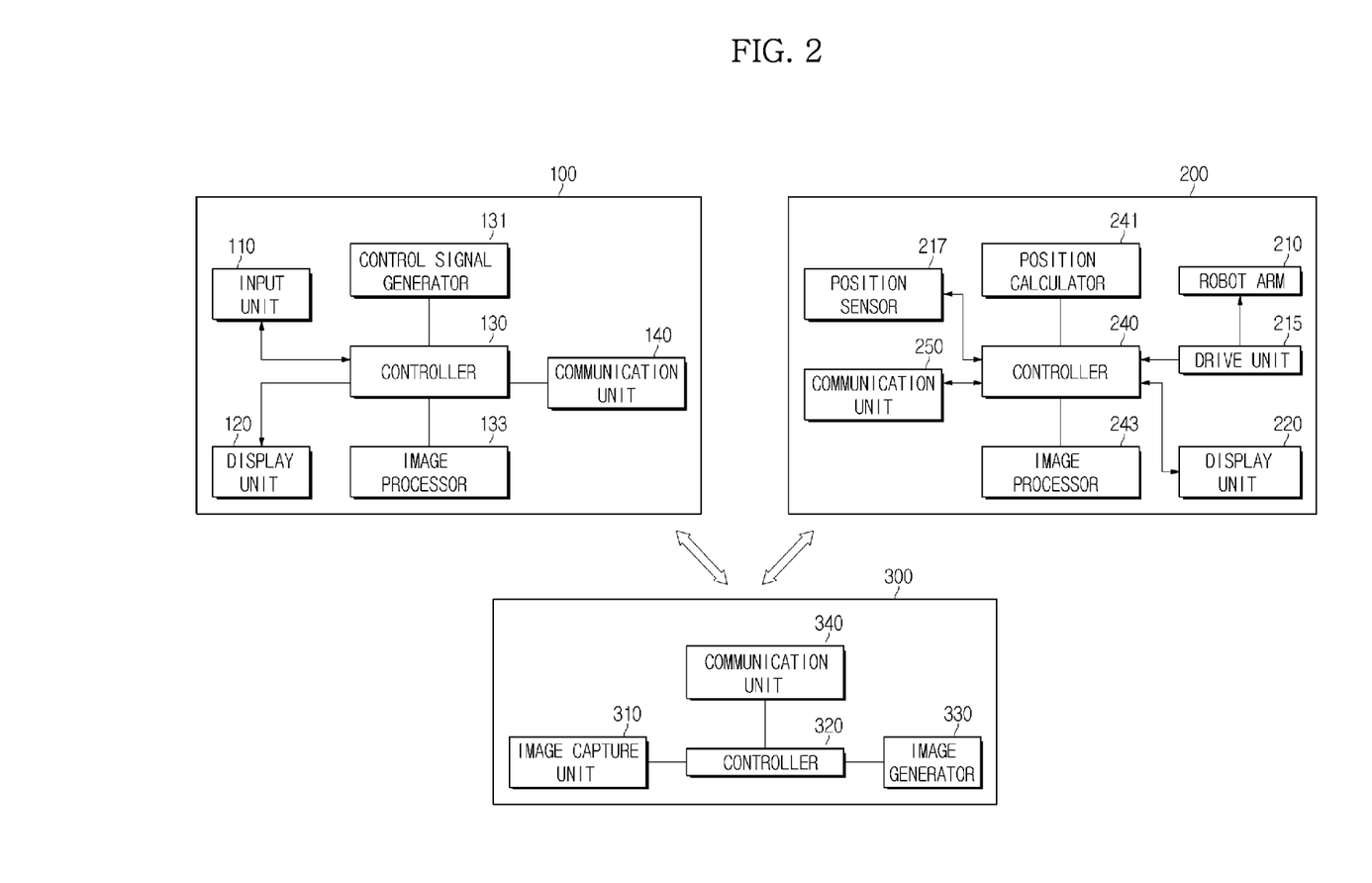
FIG. 2 is a block diagram illustrating constituent elements of a surgical robot system.
Figure 3:
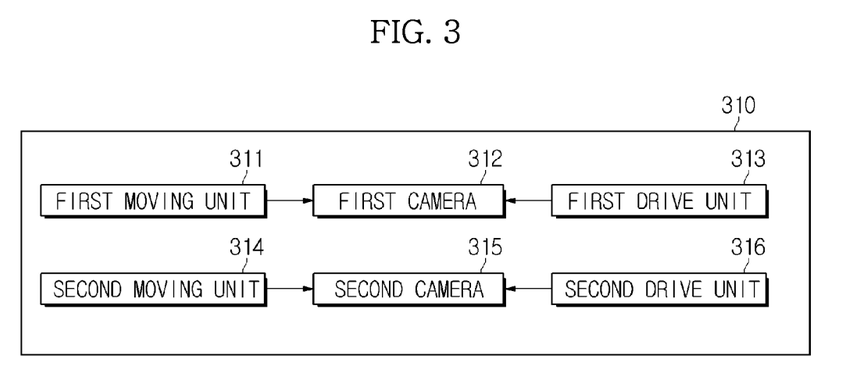
FIG. 3 is a block diagram illustrating constituent elements of an image capture unit of an imaging system.
Figure 4:
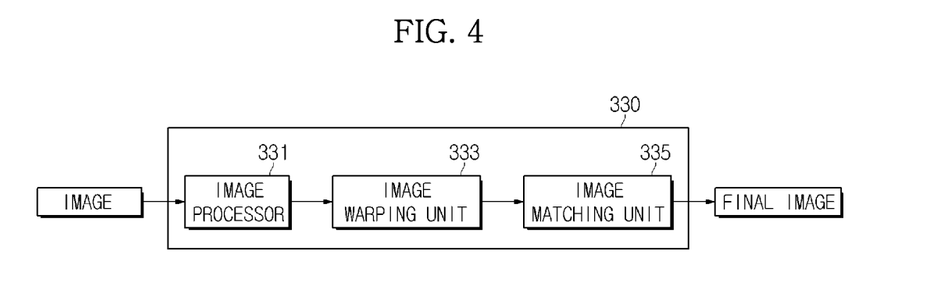
FIG. 4 is a block diagram illustrating constituent elements of an image generator of an imaging system.

FIG. 1 is a view schematically illustrating a surgical robot system. FIG. 2 is a block diagram illustrating constituent elements of a surgical robot system. FIG. 3 is a block diagram illustrating constituent elements of an image capture unit of an imaging system. FIG. 4 is a block diagram illustrating constituent elements of an image generator of an imaging system.

Referring to FIG. 1, the surgical robot system may include a slave system 200 to perform surgery on a patient P who lies on an operating table, and a master system 100 to remotely control the slave system 200 in accordance with manipulation by an operator S (e.g., a doctor). In this regard, at least one assistant A assisting the operator S may be positioned near the patient P.

In this regard, assisting the operator S may refer to assisting a surgical task while surgery is in progress, such as replacing surgical instruments, for example, but is not limited thereto. For example, a variety of surgical instruments may be used, according to the surgical task. Because the number of robot arms 210 of the slave system 200 is limited, the number of surgical instruments 230 mounted thereon at once is also limited. Accordingly, when the surgical instrument 230 is required to be replaced during surgery, the operator S instructs the assistant A positioned near the patient P to replace the surgical instrument 230. In accordance with instructions, the assistant A removes a surgical instrument 230 not in use from the robot arm 210 of the slave system 200 and mounts another surgical instrument 230' placed on a tray T on the corresponding robot arm 210.

The master system 100 and the slave system 200 may be separately arranged as physically independent devices, without being limited thereto. For example, the master system 100 and the slave system 200 may also be integrated as a single device.

As illustrated in FIGS. 1 and 2, the master system 100 may include an input unit 110 and a display unit 120.

The input unit 110 refers to an element that receives an instruction for selection of an operation mode of the surgical robot system, or an instruction for remote control of operation of the slave system 200 by the operator S. In the present embodiment, the input unit 110 may include a haptic device, a clutch pedal, a switch, and a button, but is not limited thereto. For example, a voice recognition device may be used. Hereinafter, a haptic device will be exemplarily described as an example of the input unit 110.

FIG. 1 exemplarily illustrates that the input unit 110 includes two handles 111 and 113, but the present embodiment is not limited thereto. For example, the input unit 110 may include one handle, or three or more handles.

The operator S respectively manipulates the two handles 111 and 113 using both hands, as illustrated in FIG. 1, to control an operation of the robot arm 210 of the slave system 200. Although not shown in detail in FIG. 1, each of the handles 111 and 113 may include a plurality of links and a plurality of joints.

A joint refers to a connection between two links and may have 1 degree of freedom (DOF). Here, the term "degree of freedom (DOF)" refers to a DOF with regard to kinematics or inverse kinematics. A DOF of a device indicates the number of independent motions of a device, or the number of variables that determine independent motions at relative positions between links. For example, an object in a 3D space defined by X-, Y-, and Z-axes has at least one DOF selected from the group consisting of 3 DOFs to determine a spatial position of the object with respect to a position on each axis and 3 DOFs to determine a spatial orientation of the object with respect to a rotation angle relative to each axis. More specifically, it will be appreciated that when an object is movable along each of X-, Y-, and Z-axes and is rotatable about each of X-, Y-, and Z-axes, it will be appreciated that the object has 6 DOFs.

In addition, a detector (not shown) may be mounted on the joint. The detector may detect data indicating the state of the joint, such as force/torque data applied to the joint, position data of the joint, and speed data. Accordingly, in accordance with manipulation of the input unit 110 by the operator S, the detector (not shown) may detect data of the status of the manipulated input unit 110, and the controller 130 generates a control signal corresponding to the data of the status of the input unit 110 detected by the detector (not shown) by use of a control signal generator 131 to transmit the generated control signal to a communication unit 250 in the slave system 200 via a communication unit 140. That is, the controller 130 of the master system 100 may generate a control signal according to manipulation of the input unit 110 by the operator S using the control signal generator 131 and transmit the generated control signal to the slave system 200 via the communication unit 140.

The display unit 120 of the master system 100 may display an image of a surgical region (hereinafter, referred to as "affected area") of the patient P obtained by the image capture unit 310 of the imaging system 300 which will be described later, a virtual image acquired by converting a medical image of the patient P before surgery into a 3D image, and the like. To this end, the master system 100 may include an image processor 133 to receive image data from the imaging system 300 and to output the image data to the display unit 120. In this regard, the "image data" may include an image of an affected image acquired by the image capture unit 310, a virtual image acquired by converting a medical image of the patient P before surgery into a 3D image, and the like as described above, but is not limited thereto.

The display unit 120 may include at least one monitor, and each monitor may be implemented to individually display data used for surgery. For example, when the display unit 120 includes three monitors, one of the monitors may display an affected area image acquired by the image capture unit 310, and the other two monitors may respectively display a virtual image acquired by converting a medical image of the patient P before surgery into a 3D image, and data of operation of the slave system 200 and the patient P. In this regard, the number of monitors may vary according to the type of data to be displayed.

Here, the term "data of the patient" may refer to information indicating vital signs of the patient, such as bio-data including body temperature, pulse, respiration, and blood pressure, for example. In order to provide such bio-data to the master system 100, the slave system 200, which will be described later, may further include a bio-data measurement unit including a body temperature-measuring module, a pulse-measuring module, a respiration-measuring module, a blood pressure-measuring module, and the like. To this end, the master system 100 may further include a signal processor (not shown) to receive bio-data from the slave system 200, process the bio-data, and output the resultant data to the display unit 120.

The slave system 200 may include a plurality of robot arms 210 and various surgical instruments 230 mounted on ends of the robot arms 210. The robot arms 210 may be coupled to a body 201 in a fixed state and supported thereby, as illustrated in FIG. 1. In this regard, the numbers of the surgical instruments 230 and the robot arms 210 used at once may vary according to various factors, such as diagnostic methods, surgical methods, and spatial limitations of an operating room.

In addition, each of the robot arms 210 may include a plurality of links 211 and a plurality of joints 213. Each of the joints 213 may connect links 211 and may have 1 DOF or greater.

In addition, a drive unit 215 to control motion of the robot arm 210 according to a control signal received from the master system 100 may be mounted on each of the joints of the robot arm 210. For example, when the operator S manipulates the input unit 110 of the master system 100, the master system 100 generates a control signal corresponding to the status data of the manipulated input unit 110, and transmits the control signal to the slave system 200, and a controller 240 of the slave system 200 drives the drive unit 210 in accordance with the control signal received from the master system 100, to control motion of each joint of the robot arm 210. Here, a substantial control process, such as rotation and movement in a direction corresponding to the robot arm 210, in accordance with manipulation of the input unit 110 by the operator S does not fall within the scope of the present disclosure, and thus a detailed description thereof will not be given.

Meanwhile, each joint of the robot arm 210 of the slave system 200 may move according to the control signal received from the master system 100 as described above. However, the joint may also move by external force. That is, the assistant A positioned near the operating table may manually move each of the joints of the robot arm 210 to control the location of the robot arm 210, or the like.

The surgical instruments 230, although not shown in detail in FIG. 1, may include a housing mounted on one end of the robot arm 210, a shaft extending from the housing by a predetermined length, and an end effector mounted on one end of the shaft.

In generally, the surgical instruments 230 may be classified into main surgical instruments and auxiliary surgical instruments. Here, the term "main surgical instruments" may refer to surgical instruments including end effectors, such as a scalpel or surgical needle which performs direct surgical motion, such as cutting, suturing, cauterizing, and rinsing, on the surgical region. The term "auxiliary surgical instruments" may refer to surgical instruments including end effectors, such as a skin holder which do not perform direct motions on the surgical region and assist motion of the main surgical instruments.

In addition, the end effector that constitutes the surgical instrument 230 and is directly applied to the affected area of the patient P may include a clamp, a skin holder, a suction, a scalpel, scissors, a grasper, a surgical needle, a needle holder, a stapler, a cutting blade, and the like, but is not limited thereto. Any known instruments used for surgery may also be used.

In addition, a drive wheel may be coupled to the housing. The end effector may be driven by connecting the drive wheel with the end effector via wire or the like and rotating the drive wheel. To this end, a drive unit (not shown) to rotate the drive wheel may be mounted on one end of the robot arm 210. For example, upon manipulation of the input unit 110 of the master system 100 by the operator S, the master system 100 generates a control signal corresponding to the status of the manipulated input unit 110 and transmits the control signal to the slave system 200, and the controller 240 of the slave system 200 drives the drive unit (not shown) in accordance with the control signal received from the master system 100, to control the end effector in a desired manner. However, the operating mechanism of the end effector is not necessarily constructed as described above, and various other electrical/mechanical mechanisms to realize motions of the end effector for robot surgery may be applied.

In addition, the slave system 200 according to the present embodiment may further include a position sensor 217 to detect locations of the surgical instruments 230 as illustrated in FIG. 2. The position sensor 217 may be a potentiometer, an encoder, or the like, but is not limited thereto.

The position sensor 217 may be mounted on each joint of the robot arm 210 provided with the surgical instrument. The position sensor 217 detects data regarding the status of motion of each joint of the robot arm 210. The controller 240 receives the detected data from the position sensor 217. The position and direction of the surgical instruments 230 may be calculated by use of a position calculator 241. In this regard, the position calculator 241 applies the input data to kinematics of the robot arm 210 to calculate the position and direction of the surgical instruments 230. In addition, the controller 240 may transmit the calculated data regarding the position and direction of the surgical instruments 230 to the imaging system 300, which will be described later.

As described above, the position and direction of each of the surgical instruments 230 may be estimated by detecting the status data of each of the joints of the robot arms 210 provided with the surgical instruments 230. As a result, the position and direction of the surgical instrument 230 may be efficiently estimated even when the surgical instrument 230 is located outside of a field of vision of the image capture unit 310, or a field of vision of the image capture unit 310 is blocked due to internal organs or the like.

In addition, the slave system 200 may include a display unit 220 that displays an affected area image acquired by the image capture unit 310 of the imaging system 300, a virtual image acquired by converting a medical image of the patient P before surgery into a 3D image, and the like in the same manner as in the master system 100. The slave system 200 may include an image processor 243 to receive image data from the imaging system 300 and to output the image data to the display unit 220.

According to the present embodiment as illustrated in FIG. 2, the imaging system 300 may include an image capture unit 310 that acquires a plurality of images of an affected area, an image generator 330 that detects an occluded region in each of the affected area images acquired by the image capture unit 310, removes the occluded region therefrom, warps each of the affected area images from which the occluded region is removed, and matches the resultant images to generate a final image, and a controller 320 that operates the image capture unit 310 to acquire the plurality of affected area images and inputs each of the acquired affected area images to the image generator 330 to generate the final image.

In the illustrated embodiment, the term "occluded region" may refer to a region of the affected area obscured by an object used on the patient P. Here, the "object" may be a surgical instrument 230, gauze, and the like, but is not limited thereto. That is, the "occluded region" may indicate a region of the affected area that is not readily visible.

In addition, referring to FIG. 2, the imaging system 300 according to the illustrated embodiment includes the master system 100 and the slave system 200 which are separately arranged from each other. However, this structure is exemplarily illustrated for convenience of explanation. The imaging system 300 may be integrated with the slave system 200. Alternatively, the image capture unit 310 of the imaging system 300 may be disposed in the slave system 200, and the controller 320 and the image generator 330 of the imaging system 300 may be disposed in the master system 100. However, the present embodiment is not limited thereto, and may be implemented in various ways.

In the illustrated embodiment, the image capture unit 310 of the imaging system 300 may acquire a plurality of affected area images. To this end, the image capture unit 310 of the surgical robot system may include a plurality of cameras including a first camera 312 and a second camera 315 as illustrated in FIG. 3. In this regard, the image capture unit 310 including two cameras is exemplarily illustrated in FIG. 3 for descriptive convenience, but the number of cameras contained in the image capture unit 310 is not limited thereto. In addition, the image capture unit 310 may further include a first drive unit 313 and a second drive unit 316 respectively driving the first camera 312 and the second camera 315, and the number of drive units may correspond to the number of cameras.

Figure 5:
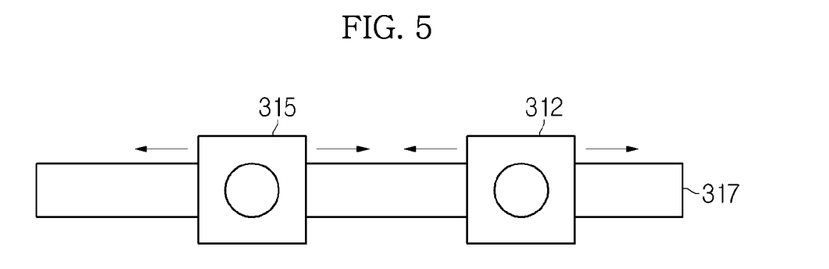
FIG. 5 is a view schematically illustrating a plurality of cameras mounted on a support member.

In addition, the first camera 312 and the second camera 315 may be mounted on a support member 317 as illustrated in FIG. 5. In this regard, a linear support member 317 is exemplarily illustrated in FIG. 5. However, the shape of the support member 317 is not limited thereto and may be embodied in various shapes, as necessary.

In addition, according to the present embodiment as illustrated in FIG. 5, the first camera 312 and the second camera 315 mounted on the support member 317 may respectively move along the support member 317 in directions designated by arrows. To this end, the image capture unit 310 may further include a first moving unit 311 and the second moving unit 314 respectively moving the first camera 312 and the second camera 315, and the number of moving units may correspond to the number of cameras.

Meanwhile, according to the illustrated embodiment, the first and second cameras 312 and 315 of the image capture unit 310 are movably mounted on the support member 317 as described above. However, the first and second cameras 312 and 315 may also be fixed to the support member 317.

In addition, in the illustrated embodiment, the first camera 312 and the second camera 315 may be depth cameras, but are not limited thereto. In this regard, the term "depth camera" refers to a camera to calculate a distance to an object by radiating laser beams or infrared (IR) light, for example, to the object or a target region (herein, an occluded region) and receiving the reflected laser beams or IR light, thereby estimating depth information of the object or the target region. A high resolution image may be acquired by use of such depth cameras, and depth of each pixel may be estimated. Thus, depth cameras may be applied to a moving object or 3D modeling.

Meanwhile, the first camera 312 and the second camera 315 may be general use cameras, such as complementary metal-oxide semiconductor (CMOS) cameras and charge coupled devices (CCDs), for example, in addition to the depth cameras. In this case, the controller 320 of the imaging system 300 estimates depth information from each of the first and second cameras 312 and 315 to the occluded regions. Here, depth information may be estimated by use of sum of absolute differences (SAD) or sum of squared differences (SSD). However, the present embodiment is not limited thereto, and any known method of estimating depth information may also be applied thereto. SAD and SSD are well known techniques in the art, and thus a detailed description thereof will not be given.

The controller of the imaging system 300 according to the illustrated embodiment, estimates depth information from each of the first and second cameras 312 and 315 to the occluded regions as described above, to determine whether to move each of the first and second cameras 312 and 315 from the current position to another position, i.e., a position corresponding to the estimated depth information. In accordance with the position of the occluded regions whether the occluded regions are positioned close to the first and second cameras 312 and 315 or close to the affected area, each of the first and second cameras 312 and 315 may be moved. Thus, a plurality of affected area images in which the positions of the occluded regions do not overlap each other may be acquired.

Figure 6:
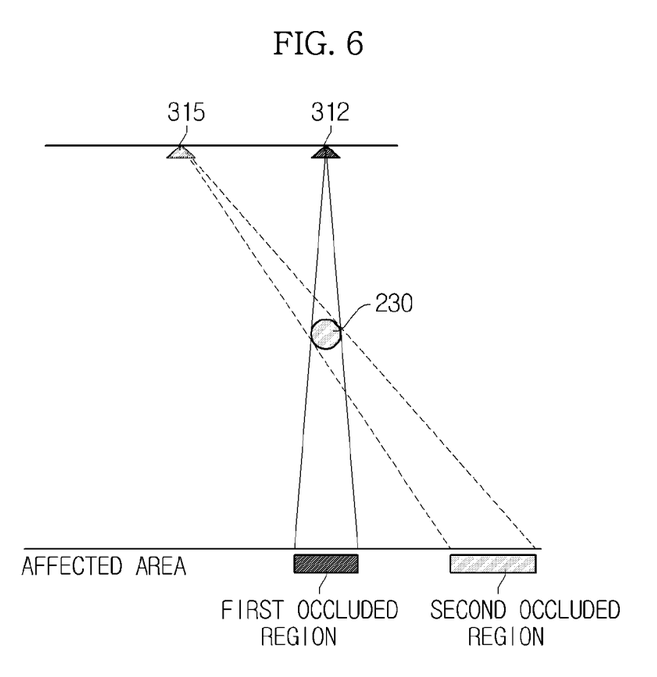
FIG. 6 is a view illustrating occluded regions generated while a surgical instrument is located between a camera and an affected area.

For example, as illustrated in FIG. 6, when the surgical instrument 230 causing the occluded region is located between each of the first and second cameras 312 and 315 and the affected area, an affected area image acquired by the first camera 312 has a first occluded region caused by the surgical instrument 230, and an affected area image acquired by the second camera 315 has a second occluded region. Here, the first and second occluded regions respectively contained in the affected area images acquired by the first and second cameras 312 and 315 are different from each other in positions and do not overlap each other.

Figure 7:
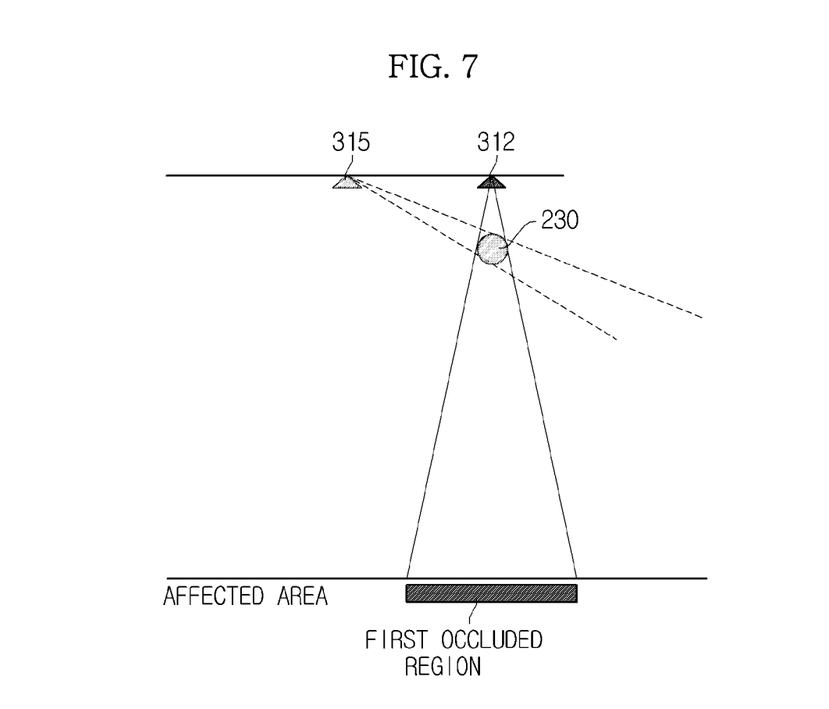
FIG. 7 is a view illustrating an occluded region generated while a surgical instrument is located close to a camera.

In addition, as illustrated in FIG. 7, when the surgical instrument 230 is positioned close to the first and second cameras 312 and 315, an affected area image acquired by the first camera 312 has a first occluded region, but an affected area image acquired by the second camera 315 does not have an occluded region.

As described above, when the surgical instrument 230 is positioned between each of the first and second cameras 312 and 315 and the affected area or close to the first and second cameras 312 and 315, occluded regions in the affected area images acquired by the first and second cameras 312 and 315 do not overlap each other. Thus, there is no need to move the first and second cameras 312 and 315.

Figure 8:
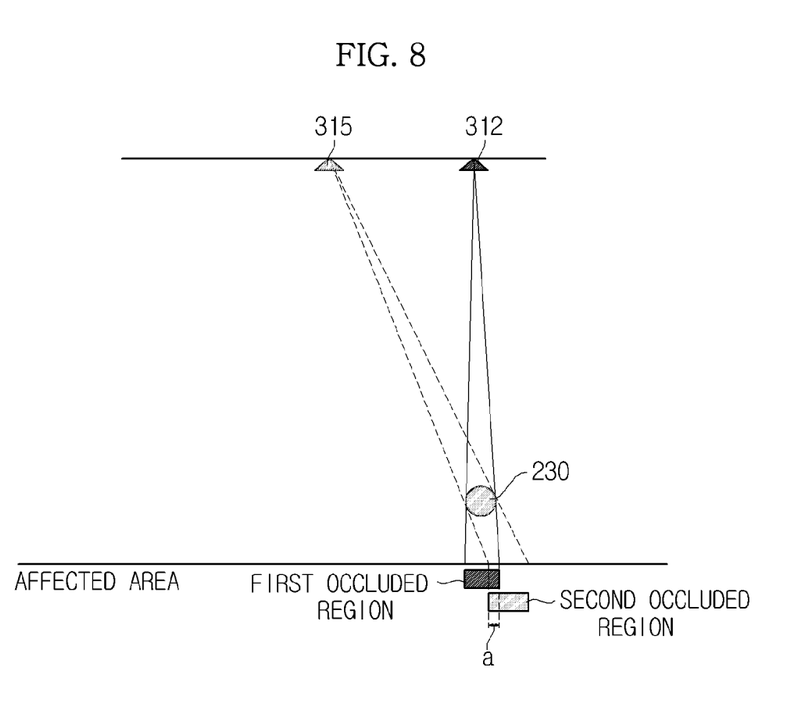
FIG. 8 is a view illustrating occluded regions generated while a surgical instrument is located close to an affected area.
Figure 9:
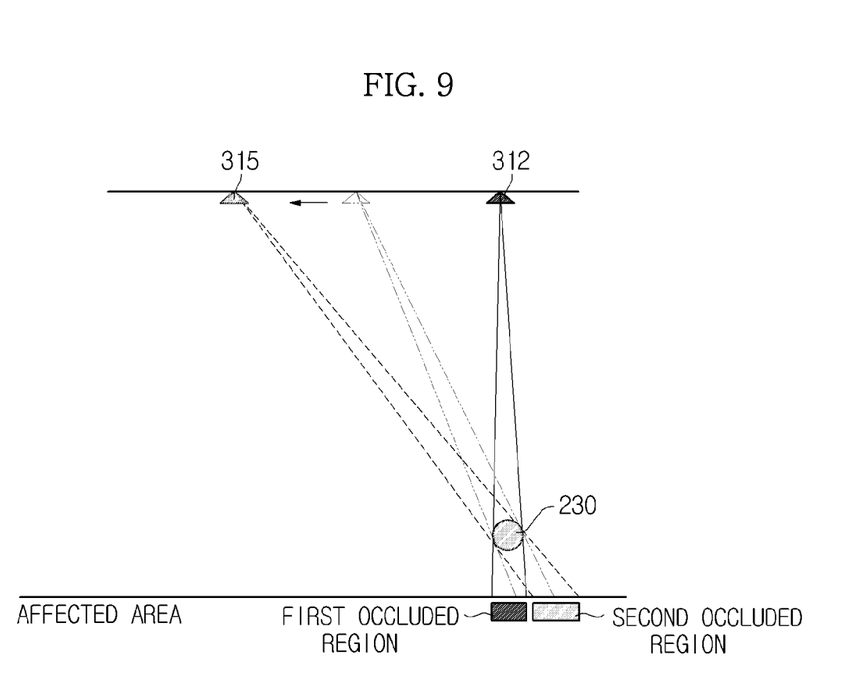
FIG. 9 is a view illustrating occluded regions, location of which changes as a camera moves.

On the other hand, as illustrated in FIG. 8, when the surgical instrument 230 is positioned close to the affected area, a first occluded region contained in an affected area image acquired by the first camera 312 overlaps a second occluded region contained in an affected area image acquired by the second camera 315 by a portion a. Because the overlap portion (portion a) of the occluded region is neither visible in the affected area image acquired by the first camera 312 nor in the affected area image acquired by the second camera 315, it is impossible to restore the overlap portion a. Accordingly, as illustrated in FIG. 9, the second camera 315 is moved in a direction designated by an arrow, so that the first occluded region does not overlap the second occluded region.

That is, according to the present embodiment, a plurality of affected area images in which the positions of the occluded regions do not overlap each other may be acquired by estimating depth information from each of the first and second cameras 312 and 315 to the surgical instrument 230 and moving the first and second cameras 312 and 315 to corresponding positions in accordance with the estimated depth information.

Although the case in which the surgical instrument 230 is positioned between each of the first and second cameras 312 and 315 and the affected area has been described, this is an example for descriptive convenience, and the occluded region may also be caused by various other factors in affected area images. It will be apparent to those having ordinary skill in the art that the present embodiment is applicable to various other cases.

In addition, the image generator 330 of the imaging system 300 according to the present embodiment may include an image processor 331, an image warping unit 333, and an image matching unit 335, as illustrated in FIG. 4.

The image processor 331 may perform image processing to detect occluded regions contained in a plurality of affected area images acquired by the image capture unit 310, and remove the detected occluded regions. In this regard, the occluded regions contained in each of the affected area images may be detected by use of various methods. For example, an occluded region caused by the surgical instrument 230 may be detected by estimating position and direction of the surgical instrument 230.

In general, the position and direction of the surgical instrument 230 that is inserted into and operates upon the patient P may be estimated using various methods as follows. First, the position and direction of the surgical instrument 230 may be calculated by detecting status data of the joint of the robot arm 210 using the position sensor 217 attached to the joint of the robot arm 210 provided with the surgical instrument 230 and applying the detected data to inverse kinematics. Second, the position and direction of the separated surgical instrument 230 may be calculated by attaching a predetermined marker to the surgical instrument 230 and separating the surgical instrument 230 from the background via recognition of the predetermined marker in the image acquired by the image capture unit 310. Third, the position and direction of the surgical instrument 230 may be calculated by extracting a blob closest to the camera, i.e., having the smallest depth data, using depth data under the condition that the bottom of a screen indicates a position closest to the camera, and spreading the extracted blob through a region growing method. In this regard, the presence of the surgical instrument 230 on the screen may be determined by use of a predetermined threshold. "Region growing" is a method of partitioning the image into basic regions having common properties and continuously integrating from regions having similar properties to regions having a wider variety of properties.

Such methods of detecting the surgical instrument 230 are well known in the art, and thus a detailed description thereof will not be given. In addition, two or more of the three methods may be simultaneously used to accurately calculate the position or direction of the surgical instrument 230, but the present embodiment is not limited thereto.

As described above, the occluded region is detected in each of the affected area images, and the detected occluded region is removed. In this regard, a portion of the affected area image from which the occluded region is removed becomes a blank region. The removed portions do not overlap each other and are located at different positions in different affected area images. That is, the position of the removed portion in the image acquired by the first camera 312 is different from that of the removed portion in the image acquired by the second camera 315. Accordingly, the removed portion of the image acquired by the first camera 312 may be replaced with a portion of the image acquired by the second camera 315 corresponding thereto. The removed portion of the image acquired by the second camera 315 may be replaced with a portion of the image acquired by the first camera 312 corresponding thereto.

The image warping unit 333 may warp a plurality of images from which the occluded regions are removed by the image processor 331. In this regard, the term "warping" refers to a method of partially or entirely transforming the image. Generally, "warping" may include transformation methods such as affine transformation, perspective transformation, and bilinear transformation, for example, but the method is not limited thereto. These methods are well known in the art, and thus a detailed description thereof will not be given.

That is, according to the illustrated embodiment, the first camera 312 and the second camera 315 are disposed to acquire a plurality of affected area images. The first camera 312 and the second camera 315 capture affected area images while being spaced apart from each other by a predetermined distance. As described above, the affected area images acquired by the first camera 312 and the second camera 315 disposed at different positions may have different forms. In this regard, the "different forms" may be obtained according to the position and angle of the camera. For example, when the first camera 312 and the second camera 315 are linearly disposed and spaced apart from each other by a predetermined distance, an affected area image acquired by the first camera 312 may have a region, which is smaller and distorted compared to a region of an affected area image acquired by the second camera 315 corresponding thereto. An affected area image acquired by the second camera 315 may have a region, which is smaller and distorted compared to a region of an affected area image acquired by the first camera 312 corresponding thereto. That is, the affected area images respectively acquired by the first and second cameras 312 and 315 may have different positions and degrees of distortion. However, this is an exemplary embodiment, and a plurality of affected area images having different degrees of distortion may be acquire according to the position and angle of the cameras.

In the illustrated embodiment, a final image is generated by matching all of the affected area images acquired by the first and second cameras 312 and 315. Thus, the affected area images having different forms are transformed to have a common form. This process may be performed by the image warping unit 333.

The image matching unit 335 matches all of the affected area images warped by the image warping unit 333 to produce a final image in which the occluded regions are restored. In this regard, image matching may be performed by various methods known in the art. For example, image matching may be performed by local feature matching by which images are matched after aligning coinciding points, or a Harris Corner detection by which images are matched to 3D spatial coordinates using external and internal parameters of a camera, and the like. However, the present embodiment is not limited thereto.

As described above, the image generator 330 of the imaging system 300 may generate a final image in which the occluded regions are restored by detecting occluded regions in each of the affected area images acquired by the first camera 312 and the second camera 315, removing the occluded regions therefrom, warping each of the affected area images from which the occluded regions are removed, and matching the warped images. That is, the removed portion, i.e., the occluded region, of the affected area image acquired by the first camera 312 is filled with a corresponding region of the affected area image acquired by the second camera 315. The removed region, i.e., the occluded region, of the affected area image acquired by the second camera 315 is filled with a corresponding region of the affected area image acquired by the first camera 312. Accordingly, an affected area image in which the occluded region is restored in real time may be generated.

In addition, in the illustrated embodiment, the imaging system 300 may further include a communication unit 340. The controller 320 of the imaging system 300 may transmit the final image generated by the aforementioned image generator 330, i.e., the affected area image in which the occluded regions are restored, to the master system 100 and the slave system 200 via the communication unit 340. The master system 100 and the slave system 200 may display the received final image on display units 120 and 220, respectively.

Figure 10:
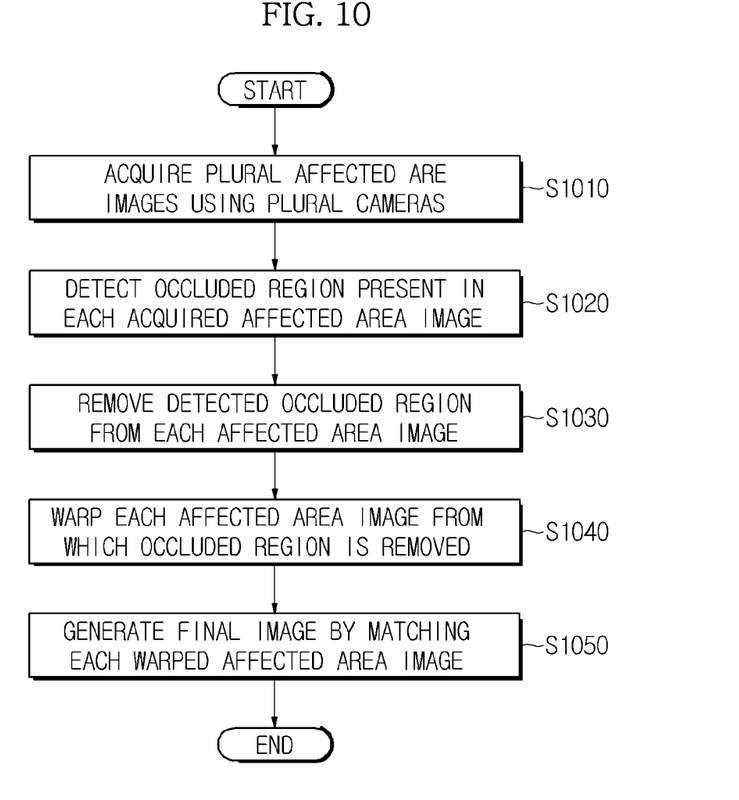
FIG. 10 is a flowchart sequentially illustrating a method of controlling a surgical robot system.

FIG. 10 is a flowchart sequentially illustrating a method of controlling a surgical robot system.

First, a plurality of affected area images is acquired using a plurality of cameras (operation S1010). In this regard, the cameras may be mounted on the support member 317 to be spaced apart from each other by a predetermined distance, as illustrated in FIG. 5. In FIG. 5, two cameras, i.e., the first and second cameras 312 and 315, are illustrated, but the number of cameras is not limited thereto. In addition, a linear support member 317 is illustrated in FIG. 5. However, this is an exemplary embodiment, and the support member 317 may have various shapes, as necessary. In addition, the cameras may be implemented to be movable along the support member 317 as illustrated in FIG. 5, but are not limited thereto. The cameras may be fixed to the support member 317.

A plurality of affected area images acquired by the plurality of cameras, which are disposed spaced apart from each other by a predetermined distance, may have various forms. That is, because the inside of the patient P does not have a planar structure but a 3D structure, and the cameras are disposed at different positions, the affected area images acquired by each of the cameras may have different forms.

Then, an occluded region is detected from each of the acquired affected area images (operation S1020). In the illustrated embodiment, the term "occluded region" may refer to a region of the affected area obscured by an object inserted into, or used for, the patient P. Here, the "object" may be a surgical instrument 230, gauze, and the like, but is not limited thereto. That is, "occluded region" may indicate a region of the affected area that is not readily visible. In addition, the occluded regions may be formed at different positions of the affected area images and do not overlap each other. For example, as illustrated in FIG. 6, because the first camera 312 and the second camera 315 are disposed to be spaced apart from each other by a predetermined distance, the first occluded region and the second occluded region may not overlap each other in the affected area images acquired by the first and second cameras 312 and 315.

However, the occluded regions of the affected area images may overlap each other according to depth of an object causing the occluded regions. The overlapping of the occluded regions may be removed by moving the camera, which will be described in detail later.

In addition, a variety of known methods may be used to detect the occluded region according to the illustrated embodiment. For example, when the occluded region is caused by the surgical instrument 230, the occluded region may be detected by estimating the current position and direction of the surgical instrument 230. In general, the current position and direction of the surgical instrument 230 that is inserted into the patient P and operates thereupon may be detected by the following methods. First, the position and direction of the surgical instrument 230 may be calculated by detecting status data of the joint of the robot arm 210 using the position sensor 217 attached to the joint of the robot arm 210 provided with the surgical instrument 230 and applying the detected data to inverse kinematics. Second, the position and direction of the separated surgical instrument 230 may be calculated by attaching a predetermined marker to the surgical instrument 230 and separating the surgical instrument 230 from the background via recognition of the predetermined marker in the image acquired by the image capture unit 310. Third, the position and direction of the surgical instrument 230 may be calculated by extracting a blob closest to the camera, i.e., having the smallest depth data, using depth data under the condition that the bottom of a screen indicates a position closest to the camera, and spreading the extracted blob through a region growing method. In this regard, the presence of the surgical instrument 230 on the screen may be determined by use of a predetermined threshold. "Region growing" is a method of partitioning the image into basic regions having common properties and continuously integrating from regions having similar properties to regions having a wider variety of properties.

Such methods of detecting the surgical instrument 230 are well known in the art, and thus a detailed description thereof will not be given. In addition, two or more of the three methods may be simultaneously used to accurately calculate the position or direction of the surgical instrument 230, but the present embodiment is not limited thereto. In addition, a method of detecting the occluded region caused by the surgical instrument 230 is described herein. However, this is an exemplary embodiment, and various known methods for detecting the occluded region may also be used according to the cause of occlusion.

When the occluded regions are not detected in this operation, the affected area images are respectively warped (operation S1040), and the warped affected area images are matched to generate a final image (operation S1050).

Then, the occluded regions are respectively removed from the affected area images (operation S1030). Here, because the positions of the occluded regions of the affected area images do not overlap each other as described above, regions of the affected area images from which the occluded regions are removed do not overlap each other, either. These regions will be filled with corresponding regions of another image in a subsequent operation.

Then, each of the affected area images from which the occluded region is removed is warped (operation S1040). Here, warping is a method of partially or entirely transforming the image. Generally, warping may include transformation methods such as affine transformation, perspective transformation, and bilinear transformation, for example, but the method is not limited thereto. These methods are well known in the art, and thus a detailed description thereof will not be given.

That is, according to the illustrated embodiment, the first camera 312 and the second camera 315 are disposed to acquire a plurality of affected area images. The first camera 312 and the second camera 315 capture affected area images in a state of being spaced apart from each other by a predetermined distance. As described above, the affected area images acquired by the first camera 312 and the second camera 315 disposed at different positions may have different forms. In the illustrated embodiment, a final image is generated by matching all of the affected area images acquired by the first and second cameras 312 and 315. Thus, the affected area images having different forms need to be transformed to have a common form.

Then, the warped affected area images are matched to produce a final image (operation S1050). In this regard, image matching may be performed by various methods known in the art. For example, image matching may be performed by local feature matching by which images are matched after aligning coinciding points, or a Harris Corner detection by which images are matched to 3D spatial coordinates using external and internal parameters of a camera, and the like. However, the present embodiment is not limited thereto.

As described above, a final image in which the occluded regions are restored may be generated according to the method of controlling the surgical robot system according to the illustrated embodiment by detecting occluded regions in each of the affected area images acquired by the first camera 312 and the second camera 315, removing the occluded regions therefrom, warping each of the affected area images from which the occluded regions are removed, and matching the warped images. That is, the removed portion, i.e., the occluded region, of the affected area image acquired by the first camera 312 is filled with a corresponding region of the affected area image acquired by the second camera 315. The removed region, i.e., the occluded region, of the affected area image acquired by the second camera 315 is filled with a corresponding region of the affected area image acquired by the first camera 312. Accordingly, an affected area image in which the occluded region is restored in real time may be generated.

Meanwhile, as described above, the occluded regions of the affected area images acquired by the first camera 312 and the second camera 315 may overlap each other according to depth of an object causing occlusion.

For example, as illustrated in FIG. 8, when the surgical instrument 230 inserted into the patient P is positioned close to the affected area, a first occluded region contained in an affected area image acquired by the first camera 312 overlaps a second occluded region contained in an affected area image acquired by the second camera 315 by a portion a. Because the overlap portion (portion a) of the occluded region is neither visible in the affected area image acquired by the first camera 312 nor in the affected area image acquired by the second camera 315, it is impossible to restore the overlap portion a. Accordingly, as illustrated in FIG. 9, the second camera 315 is moved in a direction designated by an arrow, so that the first occluded region does not overlap the second occluded region.

Figure 11:
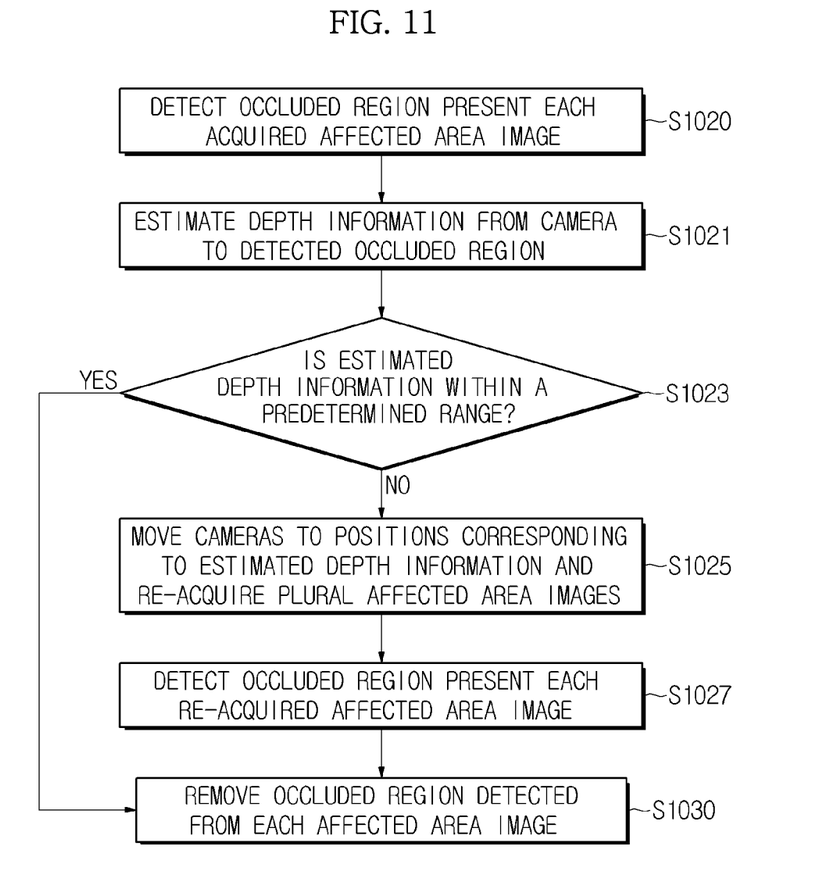
FIG. 11 is a flowchart sequentially illustrating an example of operation S1020 of FIG. 10.

To this end, according to the illustrated embodiment as illustrated in FIG. 11, the occluded regions are respectively detected from the affected area images (operation S1020), and depth information from the first and second cameras 312 and 315 to the detected occluded regions is estimated (operation S1021). Here, depth information may be estimated by use of sum of absolute differences (SAD) or sum of squared differences (SSD). However, the present embodiment is not limited thereto, and any known method of estimating depth information may also be applied thereto. SAD and SSD are well known techniques in the art, and thus a detailed description thereof will not be given.

In addition, as another method of estimating depth information, a method of estimating depth information using a depth sensor disposed at each of the first and second cameras 312 and 315 may be employed. In this regard, the term "depth sensor" refers to a sensor to calculate a distance to an object by radiating laser beams or infrared (IR) light, for example, to the object (herein, occluded region), depth of which will be estimated, and receiving the reflected laser beams or IR light, thereby estimating depth information of the object.

Then, it is determined whether the estimated depth information is within a predetermined range (operation S1023). When the estimated depth information is within the predetermined range, the occluded regions detected from the affected area images are removed (operation S1030). When the estimated depth information is not within the predetermined range, the first camera 312 and the second camera 315 are moved to positions corresponding to the estimated depth information, and then affected area images are acquired at the moved positions (operation S1025). Then, occluded regions are detected from the re-acquired affected area images (operation S1027). Then, the detected occluded regions are respectively removed from the affected area images (operation S1030).

As described above, depth information from each of the first and second cameras 312 and 315 to the occluded region is estimated, and the affected area images are acquired by moving the first and second cameras 312 and 315 according to the estimated depth information. As a result, a plurality of affected area images in which the positions of the occluded regions do not overlap each other may be acquired.

The above-described embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A method of controlling a robot, the method comprising:
    acquiring a plurality of affected area images using a plurality of cameras;
    detecting an occluded region present in each of the plurality of affected area images by detecting state data of each joint of a robot arm, the robot arm configured to mount a surgical instrument thereon;
    removing detected occluded region from each of the plurality of affected area images;
    warping each of the plurality of affected area images from which the occluded region is removed; and
    generating a final image by matching warped affected area images.

2. The method according to claim 1, wherein detected occluded regions are disposed at different positions in the plurality of affected area images.

3. The method according to claim 1, wherein the occluded region is a region at which the surgical instrument is located in each of the plurality of affected area images.

4. The method according to claim 3, wherein the detecting of the occluded region is performed by attaching a marker to the surgical instrument, and detecting the marker from each of the plurality of affected area images.

5. The method according to claim 3, wherein the detecting of the occluded region is performed by extracting a blob closest to the plurality of cameras from the each of the plurality of affected area images and spreading an extracted blob using a region growing method.

6. The method according to claim 1, wherein the detecting of the occluded region is performed by estimating depth information from the plurality of cameras to an object obscuring each of the plurality of affected areas.

7. The method according to claim 6, wherein the estimating of the depth information to the occluded region is performed by use of sum of absolute differences (SAD) or sum of squared differences (SSD).

8. The method according to claim 6, wherein the estimating of the depth information to the occluded region is performed by use of a depth sensor attached to the plurality of cameras.

* * * * *